(12) United States Patent
Leproust et al.

(10) Patent No.: US 9,163,329 B2
(45) Date of Patent: Oct. 20, 2015

(54) RNA LABELING METHOD

(75) Inventors: Emily Marine Leproust, San Francisco, CA (US); Gusti Zeiner, San Mateo, CA (US); Petula N. D'andrade, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 747 days.

(21) Appl. No.: 13/354,023

(22) Filed: Jan. 19, 2012

(65) Prior Publication Data

US 2012/0122702 A1 May 17, 2012

Related U.S. Application Data

(63) Continuation-in-part of application No. 12/944,925, filed on Nov. 12, 2010.

(51) Int. Cl.
| | |
|---|---|
| *C12Q 1/68* | (2006.01) |
| *C40B 20/02* | (2006.01) |
| *C40B 20/04* | (2006.01) |
| *C40B 70/00* | (2006.01) |

(52) U.S. Cl.
CPC .............. *C40B 20/02* (2013.01); *C12Q 1/6806* (2013.01); *C12Q 1/6837* (2013.01); *C12Q 1/6855* (2013.01); *C40B 20/04* (2013.01); *C40B 70/00* (2013.01)

(58) Field of Classification Search
CPC ........ C40B 20/02; C40B 20/04; C40B 70/00; C12Q 1/6837; C12Q 1/6855; C12Q 1/6806
USPC .................................................. 506/2–4, 16
See application file for complete search history.

(56) References Cited

U.S. PATENT DOCUMENTS

| | | |
|---|---|---|
| 2008/0045418 A1 | 2/2008 | Xia |
| 2008/0194416 A1 | 8/2008 | Chen |
| 2012/0208707 A1* | 8/2012 | Zeiner et al. ...................... 506/2 |

FOREIGN PATENT DOCUMENTS

WO     2008029295 A2     3/2008

OTHER PUBLICATIONS

"RNA Fragmentation Reagents" protocol by Ambion, 2007.*
Jiang et al. (Analyst, 2000, 125, 2176-2179).*
Galburt, et al., "Structure of a tRNA Repair Enzyme and Molecular Biology Workhorse:T4 Polynucleotide Kinase" Structure, vol. 10, 1249-1260, 2002, Elsevier Science Ltd.
Agilent Technologies, "Optimizing cRNA fragmentation for microarray experiments using the Agilent 2100 bioanalyzer", 2001, pp. 1-8.
Lui, et al., "Experimental discovery of sRNAs in Vibrio cholerae by direct cloning, 5S/tRNA depletion and parallel sequencing", Nucleic Acids Res., 2009, 37(6):e46, pp. 1-10.
Applied Biosystems, Ambion, RNA Fragmentation Reagents, www.ambion.com, 2 pages, 2008.
Li, et. al., "MicroRNA Detection by Microarray", Anal Bioanal Chem, 2009, 394:1117-24.

* cited by examiner

*Primary Examiner* — Jeremy C Flinders

(57) ABSTRACT

A method of sample analysis is provided. In certain embodiments, the method involves: a) obtaining a fragmented RNA sample comprising fragments of long RNA molecules and short RNA molecules; b) ligating an adaptor to an end of the RNA of the fragmented RNA sample to produce an adaptor-ligated sample; c) hybridizing said adaptor-ligated sample to an array of nucleic acid probes; and d) reading said array to obtain an estimate of the abundance of a long RNA in the RNA sample and an estimate of the abundance a small RNA in the RNA sample.

17 Claims, 1 Drawing Sheet

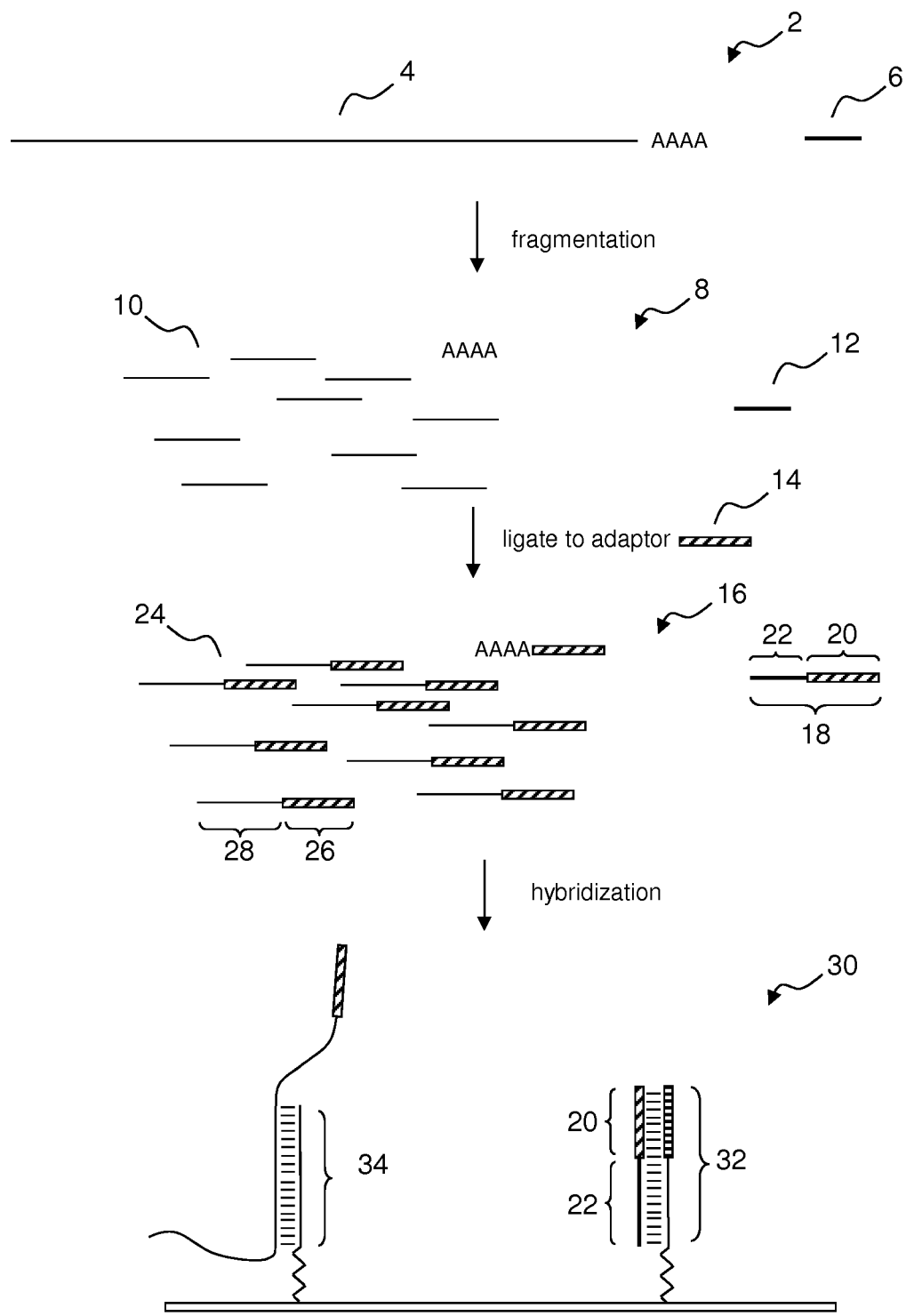

US 9,163,329 B2

RNA LABELING METHOD

CROSS REFERENCE TO RELATED APPLICATIONS

This application claims priority to the filing date of U.S. patent application Ser. No. 12/944,925, filed on Nov. 12, 2010, the disclosure of which application is herein incorporated by reference.

INTRODUCTION

Total RNA samples typically contain RNA molecules that vary in length. For example, a typical total RNA sample obtained from mammalian cells may contain mRNA molecules (which generally range in size from a few hundred bases to several kb), lincRNA molecules (which are classified as being at least 200 bases in length), 18S and 28S rRNA molecules (which are approximately 1.9 kb and 5 kb, respectively), tRNA molecules (which are generally below 100 nt in length), and a variety of small RNA molecules (e.g., short interfering RNAs, microRNAs, tiny non-coding RNAs and small modulators RNAs) some of which are in the range of 18 to 25 bases in length.

SUMMARY

A method of sample analysis is provided. In one embodiment, the method may comprise: a) obtaining a fragmented RNA sample comprising: i. fragments of long RNA molecules, wherein the long RNA molecules are at least 200 nucleotides in length; and ii. short RNA molecules of less than 200 nucleotides in length; b) ligating an adaptor to an end of the RNA of the fragmented RNA sample to produce an adaptor-ligated sample that comprises adaptor-ligated RNA molecules; c) hybridizing the adaptor-ligated sample to an array of nucleic acid probes; and d) analyzing the adaptor-ligated RNA molecules that hybridize to the array.

The hybridized adaptor-ligated RNA molecules may be analyzed by any of a variety of different methods. For example, in one embodiment, the analyzing step may comprise reading the array to obtain an estimate of the abundance of a fragmented long RNA in the RNA sample and an estimate of the abundance of a small RNA in the RNA sample.

In another embodiment, the analyzing step may comprise releasing the adaptor-ligated RNA molecules that hybridize to the array to produced released RNA. This embodiment may involve and sequencing cDNA made from the released RNA, although the released RNA may be analyzed using other methods. In particular embodiments, the adaptor may provides a binding site for a sequencing primer.

In particular embodiments, the adaptor may comprise a 2' phosphate or a 2',3'-cyclic phosphate, and the ligating is done by a eukaryotic tRNA ligase or RtcB. These embodiments may be employed if the adaptor is to be ligated to the 5' end of the fragmented sample. If the adaptor is to be ligated to the 3' end, then the adaptor may contain a 5'P or 5'OH, and could be ligated by AtRNL/RtcB to fragmented mRNAs or by T4 RNL1/2 to the 3'OH groups of miRNA.

BRIEF DESCRIPTION OF THE FIGURES

FIG. 1 schematically illustrates some of the principles of the subject method.

DEFINITIONS

The term "RNA sample", as used herein, relates a mixture of materials, typically, although not necessarily, in liquid form, containing one or more RNA molecules.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson- Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be surface-tethered, i.e., immobilized on a surface of a substrate, where the substrate can have a variety of configurations, e.g., a sheet, bead, or other structure. In certain embodiments, a probe may be present on a surface of a planar support, e.g., in the form of an array.

The phrase "surface-bound nucleic acid" refers to a nucleic acid that is immobilized on a surface of a solid substrate, where the substrate can have a variety of configurations, e.g., a sheet, bead, or other structure. In certain embodiments, the nucleic acid probes employed herein are present on a surface of the same planar support, e.g., in the form of an array.

The phrase "labeled population of nucleic acids" refers to mixture of nucleic acids that are detectably labeled, e.g., fluorescently labeled, such that the presence of the nucleic acids can be detected by assessing the presence of the label.

The term "array" encompasses the term "microarray" and refers to an ordered array presented for binding to nucleic acids and the like.

An "array," includes any two-dimensional or three-dimensional arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 5 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulsejets of either precursor units (such as nucleotide or amino acid monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other more advanced models that depend on various parameters may also be used to predict $T_m$ of oligonucleotide duplexes may also be used depending on various hybridization conditions.

As used herein, the term "$T_m$-matched" refers to a plurality of nucleic acid duplexes having $T_m$s that are within a defined range, e.g. ±5° C., ±10° C., or ±15° C.

The term "hybridization conditions" as used herein refers to hybridization conditions that are sufficient to anneal an oligonucleotide of a sufficient length to a probe that is complementary to a nucleotide sequence of the probe. The hybridization conditions provide for dissociation of duplexes that anneal over a short length of region (e.g. less than 50, less than 40, less than 30, or less than 20 contiguous nucleotides). Such conditions may differ from one experiment to the next depending on the length and the nucleotide content of the complementary region. In certain cases, the temperature for low-stringency hybridization may be 5°-10° C. lower than the calculated Tm of the resulting duplex under the conditions used.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spacially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

If a nucleic acid probe "corresponds to" or is "for" a certain RNA, the nucleic acid probe base pairs with, i.e., specifically hybridizes to, that RNA. As will be discussed in greater detail below, a nucleic acid probe for a particular RNA and the particular RNA, or complement thereof, contains at least one region of contiguous nucleotides that is identical in sequence.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed.

As used herein, the term "initial RNA sample" is an RNA sample that has not been exposed to fragmentation conditions and that contains intact RNA molecules. Such a sample may contain, for example, total cellular RNA or a total cellular RNA that has been depleted for rRNA, tRNA, or another type of RNA. An initial RNA sample contains at least one type of intact long RNA and one type of short RNA.

As used herein, the term "fragmented RNA sample" is a sample that contains fragments of RNA. A fragmented RNA sample can made from an initial RNA sample by exposing the initial RNA sample to fragmentation conditions. Fragmented RNA samples include RNA that has been extracted from FPET sample.

As used herein, the term "long RNA molecules" refers to RNA molecules that are at least 200 nt in length. Long RNA molecules include mRNA molecules, rRNA molecules and long non-coding RNA molecules such as large intergenic RNA (lincRNA) molecules.

As used herein, the term "short RNA molecules" refers to RNA molecules that are below 200 nt in length. Short RNA molecules include tRNA molecules and a variety of small non-coding regulatory RNAs generically referred herein to as "small RNAs", i.e, short interfering RNAs, microRNAs, tiny non-coding RNAs and small modulatory RNAs.

As used herein, the term "fragments of long RNA molecules" refer to RNA fragments that are obtained by fragmentation of long RNA molecules.

As used herein, the term "fragmentation conditions" refer to an environment or an agent that induces non-sequence specific fragmentation of long RNA molecules. As will be described in greater detail below, when fragmenting a sample containing both long RNA molecules and short RNA molecules, the fragmentation conditions can be tailored to provide for fragmentation of long RNA molecules without significant fragmentation of short RNA molecules.

As used herein, the term "adaptor" refers to an oligonucleotide that may be composed of any type of nucleotide. An adaptor may be, e.g., an RNA adaptor, a DNA adaptor, or it may be composed of both ribonucleotides and deoxyribonucleotides or analogs thereof. An adaptor may be labeled or unlabeled and in certain cases may be of 5-15 bases in length.

As used herein, the terms "2'-PO and 3' —OH" and "2'-phosphate and 3'-hydroxyl", in the context of a 3' terminus, refers to a nucleotide at the 3' terminus of a nucleic acid, where the sugar moiety of the nucleotide has both a phosphate group at the 2' position and a hydroxyl group at the 3' position.

As used herein, the term "2',3'-cyclic phosphate", in the context of a 3' terminus comprising 2',3'-cyclic phosphate, refers to a nucleotide at the 3' terminus of a nucleic acid, where the sugar moiety of the nucleotide has a phosphate group connected to the 2' and 3' positions, as shown below:

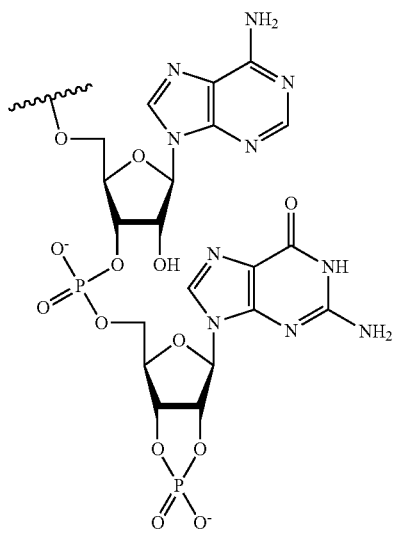

As used herein, the term "eukaryotic tRNA ligase" refers to a multifunctional enzyme that has: a) a ligase activity that catalyzes ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation; and, optionally b) a cyclic phosphodiesterase (CPD) activity that catalyzes the hydrolysis of a 2',3'-cyclic phosphate group to produce a 2'-phosphate and 3'-hydroxyl; and/or c) a kinase activity that catalyzes the phosphorylation of a 5'-hydroxyl to produce a 5'-phosphate. Wild type tRNA ligase enzymes have all three activities and are arranged as follows: a N-terminal ligase module, a central kinase module and a C-terminal 2'3'-cyclic phosphodiesterase module. Such enzymes have been identified and characterized in yeast and plants, and are expected to be present in a number of other eukaryotes, e.g., mammals and archebacteria (see, e.g., Ramirez RNA 2008 14: 1737-45; Englert Nuc. Acids Res. 2005 33: 388-399; Sawaya J. Biol. Chem. 2003 278: 43928-43928; Apostol J. Biol. Chem. 1991 266: 7445-7455; Phizicky J. Biol. Chem. 1986 261: 2978-2986; Nandakumar Mol. Cell. 2008 31: 278-286; Sugahara RNA 2007 13: 671-681; and Schutz RNA 2010 16: 621-631). As will be described in greater detail below, a eukaryotic tRNA ligase employed in a subject method may only have the ligase activity and, optionally, the kinase and/or cyclic phosphodiesterase activity. Thus, in particular cases, the eukaryotic tRNA ligase used in the method may minimally have a ligase domain having an amino acid sequence that is at least 80% to the amino acid of the ligase domain of a wild type eukaryotic tRNA ligase. The ligase domain is sufficient to catalyze ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation. The 2'-phosphate group may be removed by a 2'-phosphate group-specific specific phosphotransferase in the presence of $NAD^+$, or with a non-specific alkaline phosphatase, if necessary (Culver J. Biol. Chem. 1997: 13203-13210; Schutz RNA 2010 16: 621-631).

As used herein, the term "RtcB ligase" refers to any enzyme that has the ability to catalyze the ligation of the 3' end of an RNA having a 3' terminal 2'3'-cyclic phosphate to the 5' end of an RNA having a 5'-hydroxyl. Several examples of such enzymes (which are generically but not always referred to as "RtcB" protein in the art), are known in bacteria, archaea and eukarya (particularly in metazoan and protozoa species but not in some fungi and plants). RtcB ligases are structurally unrelated to 3'-OH RNA ligases, which ligate a 5'-phosphate-containing RNA to a 3'-hydroxyl-containing RNA, rather than ligating a 5'-hydroxyl-containing RNA to a 3' terminal 2',3'-cyclic phosphate-containing RNA. The structure, function, biochemical features and phylogenetic distribution of various RtcB ligases are described in a variety of publications, including: Tanaka et al (*RtcB is the RNA ligase component of an Escherichia coli RNA repair operon*. J. Biol. Chem. Jan. 11, 2011, e-pub ahead of print), Englert et al (*Archaeal 3'-phosphate RNA splicing ligase characterization identifies the missing component in tRNA maturation*. Proc. Natl. Acad. Sci. 2011 108: 2-7), and Okada et al (*Crystal structure of an RtcB homolog protein (PH1602-extein protein) from Pyrococcus horikoshii reveals a novel fold*. Proteins 2006 63: 1084-6)

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Sample Analysis

In general terms, certain embodiments of the method involve fragmenting an initial sample of RNA that contains intact long RNA and intact short RNA to obtain a fragmented RNA sample. The long RNA in the initial sample at least 200 nucleotides in length and may include cellular mRNA, long non-coding RNAs (such as lincRNA) and/or rRNA, for example. The defining characteristics of mRNA and rRNA are well known. lincRNA is relatively newly discovered, and is believed to be involved in regulating wide variety of processes, e.g, embryonic stem cell pluripotency, cell proliferation, cancer and chromatin structure. This class of molecules is reviewed by Gingeras (Nature Biotechnology 2009 27: 346-347). The short RNA in the initial sample of less then 200 nucleotides in length and may include, tRNA and a variety of small non-coding regulatory RNAs generically referred herein to as "small RNAs", i.e, short interfering RNAs, microRNAs, tiny non-coding RNAs and small modulatory RNAs. Small RNAs are a group of non-coding regulatory RNAs that have defined sequences and that are in the range of 18-29 nucleotides (nts) in length. Many small RNAs are approximately 19-25 nts in length.

Small RNAs are generally reviewed in Novina et al (Nature 2004 430:161-164) and may be classified in at least four groups: a) short interfering RNAs (siRNAs), b) micro-RNAs (miRNAs), c) tiny non-coding RNAs (tncRNAs) and d) small modulator RNAs (smRNAs). siRNAs are a class of double stranded RNAs of approximately 21-22 nt in length, generated from double stranded RNAs. siRNAs are thought to silence gene expression by promoting the cleavage of mRNAs. miRNAs, on the other hand, are a class of single stranded RNAs of approximately 19-25 nt in length. miRNAs appear to be evolutionary conserved and are thought to silence gene expression by inhibiting translation. tncRNAs are a class of RNAs that are about 20-22 nucleotides. tncRNAs appear to be developmentally regulated, although their function is unknown. smRNAs are double stranded RNAs involved in regulating neuron-specific gene expression in adult neurons. miRNAs are of particular interest.

The sequences of several hundred miRNAs from a variety of different species, including humans, may be found at the microRNA registry (Griffiths-Jones, Nucl. Acids Res. 2004 32:D109-D111), and at the miRBase hosted by the Faculty of Life science at the University of Manchester (UK). The sequences of all of the microRNAs deposited at the microRNA registry, including 227 microRNA sequences from humans (see Lagos-Quintana et al, Science 294:853-858 (2001); Grad et al, Mol Cell 11:1253-1263 (2003); Mourelatos et al, Genes Dev 16:720-728 (2002); Lagos-Quintana et al, Curr Biol 12:735-739 (2002); Lagos-Quintana et al, RNA 9:175-179 (2003); Dostie et al, RNA 9:180-186 (2003); Lim et al, Science 299:1540 (2003); Houbaviy et al, Dev Cell 5:351-358 (2003); Michael et al, Mol Cancer Res 1:882-891 (2003); Kim et al, Proc Natl Acad Sci USA 101:360-365 (2004); Suh et al, Dev Biol 270:488-498 (2004); Kasashima et al, Biochem Biophys Res Commun 322:403-410 (2004); and Xie et al, Nature 434:338-345 (2005)), are incorporated herein by reference. The methods and compositions described above and below may be used to detect any of the microRNAs deposited at the microRNA registry, as well as others. As will be described in greater detail below, the nucleic acid probes described herein are particularly useful for the detection of small RNAs of 18-29 nucleotides.

The initial RNA sample may contain, for example, total cellular RNA, total RNA that has been depleted for one or more types of RNA (e.g., rRNA and/or tRNA), or mRNA and small RNA, long non-coding RNA and small RNA, for example, although other combinations are contemplated.

Methods for fragmenting RNA include chemical, enzymatic or thermal fragmentation methods, protocols for which are known (see, e.g., Chandler et al, Appl. Environ. Microbiol. 2003 69:2950-2958, Guschin et al Appl. Environ. Microbiol. 1997 63:2397-2402; Kelly et al, Anal. Biochem. 2002 311:103-118, Liu et al Environ. Microbiol. 2001 3:619-629, Mehlmann et al, Anal. Biochem. 2005 347:316-323, Nguyen Nucleic Acids Res. 2000 28:3904-3909, Proudnikov Nucleic Acids Res. 2006 24:4535-4542, Small et al, Appl. Environ. Microbiol. 2001 67:4708-4716). In one embodiment, the intact RNA may be fragmented using alkali by, e.g., incubation in NaOH (e.g., 50 mM NaOH) at an elevated temperature (e.g., 55° C.) for a period of time (e.g., 10-30 minutes), as described in Liu et al (Applied and Environmental Microbiology, 2007 73: 73-82). In other embodiments, the fragmentation may be metal ion catalyzed in that the intact RNA may be incubated with a metal ion, e.g, an ion of the lanthanide series or a divalent metal ion such as $Mg^{2+}$ or $Zn^{2+}$ (which may be at a concentration of, e.g., 5 mM to 200 mM) at an elevated temperature (e.g, in the range of 50° C. to 95° C.) for a period of time e.g., 1 minute to 1 hr, as described in, e.g, Brown et al (J. Am. Chem. Soc. 2002 124: 7950-7962). For example, RNA may be fragmented by incubation with 10 mM of zinc sulfate ($ZnSO_4$) or zinc chloride ($ZnCl_2$) in 25 mM of Tris-HCl (pH 7.4) at 60° C. for 30 min, as described by Liu, supra. In an other case, the RNA may be incubated with 10 mM $ZnCl_2$ in 10 mM Tris-HCl pH7 for 15 minutes at 70° C. to produce fragments of 60 to 200 bases in length. Incubation of RNA in 40 mM Tris-acetate pH 8.1, 100 mM KOAc and 30 mM MgOA for 20-30 min at 75° C. results in fragments that are generally between 38 and 150 bases in length, as described by Mehlmann et al (Analytical biochemistry 2005 347: 316-323). All of the incubation periods described above may be altered to increase or decrease the lengths of the fragments that are obtained, as desired. The fragmented sample may contain RNA fragments that are, on average, of a length in the range of 30 to 300 nt in length, e.g., 50 to 200 nt in length.

Since fragmentation using the above methods occurs non-specifically at approximately random positions throughout the RNA, the fragmentation on average occurs in longer RNAs on a per molecule basis because the longer RNA molecules contain more potential sites for fragmentation to occur. For example, fragmentation conditions that fragment RNA to fragments of 60 to 200 bases in length should, on average, fragment an RNA molecule of 3 kb in length at approximately 15 to 50 sites without fragmenting a small RNA of approximately 18-30 nucleotides in length. Fragmentation of an RNA sample that contains long RNA molecules and short RNA molecules therefore results in a fragmented sample that contains: a) fragments of long RNA molecules and b) short RNA molecules which are largely intact. The short RNA molecules in the fragmented sample have defined ends in that the nucleotide sequences at the ends of the molecules are known, whereas the fragments of long RNA (because cleavage is not sequence specific) do not have defined ends.

After fragmentation an adaptor is ligated to an end of the RNA (i.e., the 5' end and/or the 3' end of the RNA) in the fragmented RNA sample to produce an adaptor-ligated sample. In some embodiments the adaptor may be an oligonucleotide of 5 to 20 nt in length (e.g., 6, 7, 8, 9, 10, 11 or 12 nt in length), although adaptors having a length outside of this range may also be employed, particularly if the adaptors provide binding sites for sequencing and/or PCR primers, as described below. The adaptor may be an RNA oligonucleotide or a DNA oligonucleotide. The adaptor may be ligated onto the RNA molecules of the fragmented sample using an RNA ligase, e.g., T4 RNA ligase, using any of the methods outlined in Wang et al (RNA 2007 13: 151-159) or Lockhart et al (U.S. Pat. No. 6,344,316) among many others. In particular embodiments and depending on which end of the RNA is to be ligated to the adaptor, the RNA in the fragmented may be treated using a phosphatase such as, e.g, calf intestinal phosphatase or a kinase such as T4 polynucleotide kinase to provide an appropriate terminal group (e.g., a 3'-OH) for ligation. Again, depending on how which end of the RNA is being ligated to the adaptor, the 3' end or the 5' end of the adaptor may be modified so one end of the adaptor will not ligate. In particular embodiments, the treatment may be done in the absence of ATP, thereby preventing the production of, e.g., a phosphate on the 5' end of the fragments. In some embodiments, the ligation may be done using a eukaryotic tRNA ligase or RtcB, in which case the adaptor have a 2'-PO and 3'-OH or a 2',3'-cyclic phosphate. In these embodiments, the 5' end of the adaptor may be blocked or labeled. Depending on how the ligation step is performed, the RNA molecules produced in the ligation step may have an adaptor at the 3' end, and adaptor at the 5' end, or an adaptor at both the 3' and 5' ends (which adaptor may be the same or different).

As will be discussed in greater detail below, in certain embodiments, the RNA may be labeled at any point in the method, e.g., prior to ligation or after ligation, methods for which are known. In some embodiments, the adaptor may contain a label and, as such, the ligation of the adaptor to the RNA labels the RNA.

Suitable labels include fluorescent dyes that include xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2', 7'-dimethoxyfluorescein (JOE or J), N,N,N', N'-tetramethyl-6-carboxyrhodamine (TAMRA or T), 6-carboxy-X-rhodamine (ROX or R),5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in some applications include: pyrene, coumarin, diethylaminocoumarin, FAM, fluorescein chlorotriazinyl, R110, eosin, JOE, R6G, tetramethylrhodamine, TAMRA, lissamine, ROX, napthofluorescein, Texas red, napthofluorescein, Cy3, and Cy5, etc.

Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002).

In certain cases, the RNA may by labeled using the Universal Linkage System (ULS™, KREATECH Diagnostics; van Gijlswijk et al Universal Linkage System: versatile nucleic acid labeling technique Expert Rev. Mol. Diagn. 2001 1:81-91). In brief, ULS™ is based on the stable binding properties of platinum (II) to nucleic acids. The ULS molecule consists of a monofunctional platinum complex coupled to a detectable molecule of choice. Alternative methods may be used for labeling the RNA, for example, as set out in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). In embodiments in which a ULS labeling protocol is employed, the labeled RNA may be fragmented as part of the ULS labeling method, which may result in the RNA fragments discussed above.

After adaptor ligation, the adaptor-ligated sample is hybridized to an array of nucleic acid probes. The hybridized RNA molecules may be analyzed using a variety of different methods. In one embodiment, the hybridized RNA molecules are released from the RNA prior to analysis, e.g., by heating or another suitable method. In these embodiments, the method may be used to select a particular sub-population of RNA molecules from a larger population, e.g., total RNA, for future analysis. In particular embodiments, the released RNA molecules may be made into cDNA and sequenced. In some cases, the cDNA may be amplified by PCR prior to being sequenced. Methods for the production of cDNA (e.g., double stranded cDNA) from RNA, and for performing PCR, are well known. In particular embodiments, an adaptor used may provide a primer binding site for amplifying and/or sequencing the cDNA next to the adaptor. In particular cases, the sequence of an adaptor may in certain cases be compatible with one or more next-generation sequencing platforms. In certain embodiments, the released products may be clonally amplified in vitro, e.g., using emulsion PCR or by bridge PCR, and then sequenced using, e.g., a reversible terminator method (Illumina and Helicos), by pyrosequencing (454) or by sequencing by ligation (SOLiD). Examples of such methods are described in the following references: Margulies et al (Genome sequencing in microfabricated high-density picolitre reactors". Nature 2005 437: 376-80); Ronaghi et al (Real-time DNA sequencing using detection of pyrophosphate release Analytical Biochemistry 1996 242: 84-9); Shendure (Accurate Multiplex Polony Sequencing of an Evolved Bacterial Genome Science 2005 309: 1728); Imelfort et al (De novo sequencing of plant genomes using second-generation technologies Brief Bioinform. 2009 10:609-18); Fox et al (Applications of ultra-high-throughput sequencing. Methods Mol. Biol. 2009; 553:79-108); Appleby et al (New technologies for ultra-high throughput genotyping in plants. Methods Mol. Biol. 2009; 513:19-39) and Morozova (Applications of next-generation sequencing technologies in functional genomics. Genomics. 2008 92:255-64), which are incorporated by reference for the general descriptions of the methods and the particular steps of the methods, including all starting products, reagents, and final products for each of the steps.

If the adaptor is labeled, then the array may be read to obtain an estimate of the abundance of a long RNA in the initial RNA sample and an estimate of the abundance of a short RNA in the initial RNA sample. In particular embodiments, the array is read to independently obtain estimates of the abundance of a plurality of (i.e., at least 10, at least 100, at least 500, at least 1,000, at least 10,000, or at least 50,000 up to at least 100,000) different long RNAs and different short RNAs in the initial RNA sample. The nucleic acid probes that are for detection of the small RNA contain a sequence that is complementary to the short RNA as well as a sequence that is complementary to the adaptor sequence, while the nucleic acid probes that are for detection of the long RNA contain a sequence that is complementary to the long RNA but not a sequence that is complementary to the adaptor.

Specifically, after ligation of the adaptor, the adaptor-ligated sample may contain: i. adaptor-ligated short RNA that contain an adaptor portion and a short RNA portion; and ii. adaptor-ligated long RNA fragments comprising an adaptor portion and a long RNA portion. The adaptor-ligated sample is hybridized with array that contains: a i. a first nucleic acid probe that contains a nucleotide sequence that is complementary to both the adaptor portion and of said the RNA portion of the adaptor-ligated short RNA; and ii. a second probe that contains a nucleotide sequence that is complementary to the long RNA portion of the adaptor-ligated long RNA but not the adaptor portion of said adaptor-ligated long RNA.

The addition of the adaptor to the short RNA and inclusion of the adaptor sequence in the nucleic acid probe effectively increases length of the complementary region between the short RNA and the complementary probe (which may be as long as 25-40 base pairs as opposed to 18-25 base pairs without the adaptor), thereby increasing the $T_m$ of the hybrid formed between the short RNA and corresponding probe. This allows hybridization to be done at a higher temperature, and also allows a majority of the probes on the array (i.e., probes corresponding to long RNAs as well as probes corresponding to short RNAs) to be temperature matched. Since the long RNAs are fragmented approximately randomly, the addition of the adaptor to the long RNAs is at random positions and, as such, there is no need or advantage for the probes corresponding to the long RNAs to contain a sequence that is complementary to the adaptor.

FIG. 1 illustrates some of the principles of one embodiment of the subject method. In the embodiment shown in FIG. 1, a fragmented RNA sample is obtained by fragmenting the RNA of initial RNA sample 2 that contains long RNA molecules 4 that are at least 200 nucleotides in length (as shown, long RNA 4 is an mRNA although other long RNAs could be employed) and short RNA molecules 6 that are of less then 200 nucleotides in length. The resultant fragmented RNA sample 8 contains: i. fragments of the long RNA molecules 10 and intact short RNA 12. After fragmentation and optional treatment with a kinase or phoshpatase, adaptor 14 (which may be labeled) is added to an end of the RNA of fragmented RNA sample 8 to produce adaptor-ligated sample 16. As shown, the adaptor is ligated to the 3' end of the RNA. However, the adaptor may also be added to the 5' end of the RNA. Adaptor-ligated sample 16 contains: i. adaptor-ligated short RNA 18 that comprises an adaptor portion 20 and a short RNA portion 22; and ii. adaptor-ligated long RNA fragments 24 comprising an adaptor portion 26 and a long RNA portion 28. The adaptor-ligated sample is then hybridized to array of nucleic acid probes 30. Array 30 contains i. a first nucleic acid probe that comprises a nucleotide sequence 32 that is complementary to both adaptor portion 22 and the short RNA portion 20 of the adaptor-ligated short RNA; and ii. a second probe that comprises a nucleotide sequence 34 that is complementary to long RNA portion 28 of adaptor-ligated long RNA 24 but not adaptor portion 26 of adaptor-ligated long RNA 24. While the lengths of the complementary sequences may vary greatly depending on the length of the short RNA to be detected and the length of the adaptor, in certain embodiments the complementary sequences are in the range of 25-50 nucleotides, e.g, in the range of 28-40 nucleotides. The array may then be read to obtain an estimate of the abundance of a long RNA in the RNA sample and an estimate of the abundance of a small RNA in the RNA sample. Methods for hybridizing samples to an array, for reading arrays, and for processing data obtained from arrays are known and may be readily adapted for use in this method.

The presence of a sequence that is complementary to the adaptor in a probe increases the melting temperature of a duplex formed by the adaptor-ligated short RNA and the nucleic acid probe. The ability to increase the melting temperature of such duplexes, in some embodiments, allows arrays having more favorable binding characteristics (as compared to arrays made using nucleic acid probes that do not contain the adaptor-complementary sequences) to be designed and made.

In other words, the use of nucleic acid probes containing an adaptor-complementary sequence allows a set of nucleic acid probes for detecting short RNAs to that have a lower $T_m$ spread (and, in certain embodiments, higher average $T_m$) than a set of nucleic acid probes that do not contain the adaptor complementary sequence. In one exemplary embodiment, the use of such arrays allows highly stringent hybridization conditions to be employed. For example, fewer ions, a higher hybridization temperature, a higher wash temperature or a extended wash period may be employed in hybridizing the subject arrays with a sample containing labeled polynucleotides, as compared to arrays containing otherwise identical nucleic acid probes that do not contain adaptor complementary sequence. For example, in hybridization of a subject array, salt concentration may be decreased or hybridization temperature may be increased in either the hybridization buffer employed or wash buffer employed, or both the hybridization and wash buffers employed for hybridization, as compared to an otherwise identical array that does not contain nucleic acid probes having the adaptor complementary sequence. A prolonged wash after the hybridization incubation may also be employed in the subject hybridization methods. The use of such probes effectively increases the $T_m$s of the probes for the small RNAs, without increasing the $T_m$s of the long RNAs, thereby allowing use of a single hybridization condition that is sufficiently stringent to allow specific hybridization of both types of RNA.

Arrays

A subject array may contain a plurality of features (i.e., at least 100, at least 1,000 at least 10,000, at least 50,000, at least 100,000 or more different features, etc.), each containing a different nucleic acid probe for detecting an RNA. A subject array contains at least 1 probe for detecting a long RNA and at least one probe for detecting an adaptor ligated short RNA. In certain embodiments, at least 5%, at least 10% or at least 20% of the nucleic acid probes of an array contain an adaptor-complementary sequence and are for detecting adaptor-ligated short RNAs. In certain embodiments, the probes that are for detecting the adaptor-ligated short RNAs are generally of the formula V-A, where V is a region of variable sequence and A is the adaptor-complementary sequence. Between the different probes that are for detecting the adaptor-ligated short RNAs, the V are complementary to the different short RNAs. The probes that are for detecting the adaptor-ligated long RNAs fragments are generally of the formula Z, where Z is a region of variable sequence. Between the different probes that are for detecting the adaptor-ligated ling RNAs, the Z region are complementary to the different long RNAs. Probes may be tethered to the surface of a substrate by either end.

In certain embodiments, the probes are surface-bound nucleic acid probes, where such a nucleic acid probe is bound, usually covalently but in certain embodiments non-covalently, to a surface of a solid substrate, i.e., a sheet, bead, or other structure. In certain embodiments, a surface-bound nucleic acid probe may be immobilized on a surface of a planar support, e.g., as part of an array.

Different nucleic acid probes are present in different features of an array, i.e., spatially addressable areas of an array. In many embodiments a single type of nucleic acid probe is present in each feature (i.e., all the nucleic acid probes in the feature have the same sequence).

In certain embodiments, a subject array may contain a plurality of subject nucleic acid probes that correspond to (i.e., may be used to detect) a corresponding plurality of polynucleotides. In particular embodiments, the subject arrays may contain nucleic acid probes for detecting at least a portion of all of the identified large and small RNAs of a particular organism.

In general, methods for the preparation of nucleic acid arrays, particularly oligonucleotide arrays, are well known in the art (see, e.g., Harrington et al., Curr Opin Microbiol. (2000) 3:285-91, and Lipshutz et al., Nat. Genet. (1999) 21:20-4) and need not be described in any great detail. The subject nucleic acid arrays can be fabricated using any means available, including drop deposition from pulse jets or from fluid-filled tips, etc, or using photolithographic means. Either polynucleotide precursor units (such as nucleotide monomers), in the case of in situ fabrication, or previously synthesized polynucleotides can be deposited. Such methods are described in detail in, for example U.S. Pat. Nos. 6,242,266, 6,232,072, 6,180,351, 6,171,797, 6,323,043, etc., the disclosures of which are herein incorporated by reference.

In certain embodiments an array may have probes of a similar $T_m$s relative to the RNAs in the adaptor-ligated sampe. The spread of $T_m$s of such arrays may be less than about 10° C., less than about 5° C., or less than about 2° C., for example. The spread of $T_m$s of an array may be theoretically determined, or, in certain embodiments, experimentally determined.

Kits

Also provided by the subject invention are kits for practicing the subject methods, as described above. The subject kits contain at least a subject array, ligation reagents including an RNA ligase; and an adaptor, as described above. The kit may also contain reagents for isolating RNAs from a cell, reagents for labeling a RNA, reagents for hybridizing labeled small RNAs to an array, a control RNA, and reagents for fragmenting RNA etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods may be employed in a variety of diagnostic, drug discovery, and research applications that include, but are not limited to, diagnosis or monitoring of a disease or condition (where the expression of short and/or long RNAs provide a marker for the disease or condition), discovery of drug targets (where a short and/or long RNA is differentially expressed in a disease or condition and may be targeted for drug therapy), drug screening (where the effects of a drug are monitored by assessing the level of a short and/or long RNA), determining drug susceptibility (where drug susceptibility is associated with a particular profile of a short and/or long RNA) and basic research (where is it desirable to identify the presence of short and/or long RNAs in a sample, or, in certain embodiments, the relative levels of a particular short and/or long RNAs in two or more samples).

In certain embodiments, relative levels of small short and/or long RNAs in two or more different small RNA samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the short and/or long RNA profiles of two or more different samples may be compared to identify short and/or long RNAs that are associated with a particular disease or condition (e.g., a short and/or long RNA that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

Accordingly, among other things, the instant methods may be used to link the expression of certain genes to certain physiological events.

The following example is offered by way of illustration and not by way of limitation.

EXAMPLE

Total RNA Labeling Method

A sample of 100 ng of purified human placenta total RNA was end-labeled with a Cy5-labeled RNA adaptor as follows.

A sample of 100 ng total RNA was dephosphorylated with alkaline phosphatase for 30 minutes at 37° C. in a 10 µl reaction of the following composition: 100 ng RNA, 50 mM Tris-HCl (pH 9.0), 1 mM $MgCl_2$, 1 U/µl Calf Intestinal Alkaline Phosphatase. The RNA was then fragmented by heating the reaction mixture at 95° C. for 10 min and chilled on ice. These fragmentation conditions can be adjusted depending on the desired level of fragmentation. Approximately 5-10 minutes are optimal for fragmenting long RNAs without significantly fragmenting the small RNAs like miRNAs. Fragmentation for 2-20 minutes at 95° C. gave acceptable but not optimal results. The fragmented RNA was phenol extracted, ethanol precipitated, and resuspended in 5 µl of RNase-free water.

To remove phosphoryl groups from the 3'-end of the fragments, the fragmented RNA was treated for 1 hour at 37° C. with T4 Polynucleotide Kinase (3'-phosphatase plus) in a 20 µl reaction containing 5 µl RNA, 70 mM Tris-HCl pH 7.5, 10 mM $MgCl_2$, 5 mM dithiothreitol, 1 U/µl T4 PNK. 3 µl of 100% DMSO are added to the reaction mixture and the T4 PNK is heat-inactivated at 65° C. for 20 minutes. The reaction was chilled on ice after heating. A total of 7 µl of ligation mix are then added to the sample, containing 50 mM Tris-HCl (pH 7.5), 10 mM $MgCl_2$, 10 mM dithiothreitol, 3 µl 10 mM ATP, 1 µl of 1 mM Cy5-RNA adaptor, 30 U T4 RNA ligase.

The Cy5-RNA extender is a 10mer RNA oligonucleotide with a 5'-phosphate and a 3'-Cy5 (5'-P-AUGAUUCUAU-Cy5-3'; SEQ ID NO:1). The modification at the 3'-end prevents usage of this end during the ligation step. Adaptors of length 6, 8, 10, and 12 nucleotides were tested. The 8mer and 10mer are optimal, although the others still work. Adaptors labeled with Cy3 have also been used with equal success.

The ligation reaction (30 µl) was then incubated for 2 hours at 16° C. 20 µl of RNase-free water are added to the sample for a total volume of 50 µl and then loaded onto a Micro Bio-spin 6 column for purification. The flow-through from the column is completely dried in a vacuum concentrator at 45 to 55° C. Labeled RNA was then resuspended in RNase-free water for array hybridization.

Alternatively, the method may involve the ligation of cyanine-labeled adaptors to the 5' termini of fragmented longer RNAs and miRNAs. For example, longer RNAs can first be fragmented at >50° C. in the presence of 10 mM MgCl or another divalent cation for 1-30 minutes, followed by cooling the fragmented RNA/miRNA mixture to 37° C., adding 0.1-10 picomoles of AtRNA ligase (a mutant form without CPD activity, which is unable to repair the 2',3'-cyclic-phosphate termini of the long RNA fragments and thus the 3' termini of both fragmented longer RNAs and miRNAs are not substrates for AtRNL) and a molar excess of Cy3-8-mer-[2'PO,3'OH] adaptor in the presence of 1 mM GTP and 1 mM ATP. AtRNL will first phosphorylate the 5'-OH groups of the fragmented longer RNAs (this phosphorylation reaction is virtually complete 10 minutes after assembling the reaction mixture and incubating at 37° C.), followed by ligation of the now-phosphorylated longer RNA fragments and phosphorylated miRNAs to the 5'-Cy3-labeled adaptor; this ligation will be >95% complete in 15-30 minutes. These 5'-Cy3-labeled fragmented mRNAs and miRNAs can then be diluted directly into microarray hybridization buffer, quickly denatured by heating, then hybridized directly to a microarray containing probes complementary to the labeled mRNA and miRNAs.

What is claimed is:

1. A method of sample analysis comprising:
   a) obtaining a fragmented RNA sample comprising:
      i. fragments of long RNA molecules, wherein the long RNA molecules are at least 200 nucleotides in length; and
      ii. short RNA molecules of less than 200 nucleotides in length;
   b) ligating an adaptor to an end of the RNA of said fragmented RNA sample to produce an adaptor-ligated sample that comprises adaptor-ligated RNA molecules comprising:
      i. adaptor-ligated short RNA comprising an adaptor portion and a short RNA portion; and
      ii. adaptor-ligated long RNA fragments comprising an adaptor portion and a long RNA portion;
   c) hybridizing said adaptor-ligated sample to a plurality of nucleic acid probes comprising:
      i. a first nucleic acid probe that comprises a nucleotide sequence that is complementary to both said adaptor portion and said short RNA portion of said adaptor-ligated short RNA; and
      ii. a second probe that comprises a nucleotide sequence that is complementary to the long RNA portion of said adaptor-ligated long RNA but not said adaptor portion of said long RNA; and
   d) analyzing the adaptor-ligated RNA molecules that hybridize to said probes.

2. The method of claim 1, wherein step d) comprises measuring the abundance of a fragmented long RNA in said RNA sample and the abundance of a small RNA in said RNA sample.

3. The method of claim 1, wherein step d) comprises releasing the adaptor-ligated RNA molecules that hybridize to said probes to produced released RNA, and sequencing the released RNA.

4. The method of claim 3, wherein said adaptor provides a binding site for a sequencing primer.

5. The method of claim 1, wherein said adaptor comprises a 2' phosphate or a 2',3'-cyclic phosphate, and said ligating is done by a eukaryotic tRNA ligase or RtcB.

6. The method of claim 1, wherein said fragmented RNA sample is made by exposing an initial RNA sample comprising intact long RNA and short RNA to fragmentation conditions.

7. The method of claim 6, wherein said exposing comprises contacting said initial RNA sample with a divalent cation at a temperature of at least 50° C.

8. The method of claim 6, wherein said initial RNA sample comprises total cellular RNA from which tRNA and rRNA has been removed.

9. The method of claim 1, wherein said short RNA molecules comprise small RNA molecules selected from the group consisting of short interfering RNA (siRNA) molecules, microRNA (miRNA) molecules, tiny non-coding RNA (tncRNA) molecules or small modulatory RNA (smRNA) molecules.

10. The method of claim 1, wherein said long RNA molecules comprise lincRNA molecules or mRNA molecules.

11. The method of claim 1, wherein said adaptor is in the range of 6 to 12 nucleotides in length.

12. The method of claim 1, further comprising treating said fragmented RNA sample with a polynucleotide kinase or a phosphatase in the absence of ATP prior to said ligating step b), to produce ligatable RNA that lacks a 5' phosphate in said fragmented RNA sample.

13. The method of claim 1, wherein the RNA of said fragmented RNA sample is labeled prior to or after said ligating step b).

14. The method of claim 1, wherein said adaptor is a labeled adaptor.

15. The method of claim 1, wherein step c) comprises hybridizing said adaptor-ligated sample to an array comprising a plurality of nucleic acid probes.

16. The method of claim 1, wherein said method comprises ligating an adaptor to the 5' end of the RNA of said fragmented RNA sample.

17. The method of claim 12, wherein said method comprises ligating an adaptor to the 3' end of the RNA of said fragmented RNA sample.

* * * * *

SEQUENCE LISTING

```
<160> NUMBER OF SEQ ID NOS: 1

<210> SEQ ID NO 1
<211> LENGTH: 10
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_difference
<222> LOCATION: 1
<223> OTHER INFORMATION: 5'-terminal phosphate
<220> FEATURE:
<221> NAME/KEY: misc_difference
<222> LOCATION: 10
<223> OTHER INFORMATION: 3'-terminal Cy5 tag

<400> SEQUENCE: 1
augauucuau                                                          10
```